(12) United States Patent
Kawamura

(10) Patent No.: US 11,604,188 B2
(45) Date of Patent: Mar. 14, 2023

(54) DETECTION APPARATUS, DETECTION SUBSTRATE, AND DETECTION METHOD

(71) Applicant: Panasonic Intellectual Property Management Co., Ltd., Osaka (JP)

(72) Inventor: Tatsurou Kawamura, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 292 days.

(21) Appl. No.: 16/905,915

(22) Filed: Jun. 19, 2020

(65) Prior Publication Data

US 2020/0319177 A1 Oct. 8, 2020

Related U.S. Application Data

(63) Continuation of application No. PCT/JP2019/005590, filed on Feb. 15, 2019.

(30) Foreign Application Priority Data

Mar. 16, 2018 (JP) .............................. JP2018-049021

(51) Int. Cl.
*G01N 33/543* (2006.01)
*G01N 21/64* (2006.01)
(Continued)

(52) U.S. Cl.
CPC ... *G01N 33/54373* (2013.01); *G01N 21/6428* (2013.01); *G01N 33/553* (2013.01);
(Continued)

(58) Field of Classification Search
CPC ......... G01N 33/54373; G01N 21/6428; G01N 33/553; G01N 33/582; G01N 2021/6439;
(Continued)

(56) References Cited

U.S. PATENT DOCUMENTS

2008/0219893 A1 9/2008 Ohtsuka
2013/0260479 A1 10/2013 Chou et al.

FOREIGN PATENT DOCUMENTS

JP 2001-133455 5/2001
JP 2008-216046 9/2008
(Continued)

OTHER PUBLICATIONS

Li et al., "Sensitive detection of carcinoembryonic antigen using surface plasmon resonance biosensor with gold nanoparticles signal amplification", Talanta, 2015, p. 143-149 (Year: 2015).*
(Continued)

*Primary Examiner* — Samuel P Siefke
*Assistant Examiner* — Henry H Nguyen
(74) *Attorney, Agent, or Firm* — Wenderoth, Lind & Ponack, L.L.P.

(57) ABSTRACT

A detection apparatus includes: a substrate; a metal nanostructure on a surface of the substrate and on which immobilized antibodies having a property of binding with a detection object substance are immobilized, the metal microstructure generating a surface plasmon by being irradiated with excitation light; an introducer that introduces labeled antibodies having a property of binding with the detection object substance and labeled with a fluorescent material, and a test solution containing the detection object substance into the metal nanostructure; a light source that irradiates the metal nanostructure with the excitation light from the back surface side of the substrate; and a photodetector that detects the detection object substance based on fluorescence generated from the fluorescent material in response to irradiation of the excitation light. The metal nanostructure includes a light transmissive portion that transmits, to the surface side of the substrate, the excitation light emitted from the back surface side thereof.

6 Claims, 11 Drawing Sheets

(51) Int. Cl.
  *G01N 33/553* (2006.01)
  *G01N 33/58* (2006.01)
  *G02B 5/00* (2006.01)
(52) U.S. Cl.
  CPC ........... *G01N 33/582* (2013.01); *G02B 5/008* (2013.01); *G01N 2021/6439* (2013.01)
(58) Field of Classification Search
  CPC .... G01N 21/648; G02B 5/008; G02B 5/1861; B82Y 30/00
  See application file for complete search history.

(56) References Cited

FOREIGN PATENT DOCUMENTS

| | | |
|---|---|---|
| JP | 2010-019765 | 1/2010 |
| JP | 2014-211320 | 11/2014 |
| JP | 2015-212674 | 11/2015 |

OTHER PUBLICATIONS

International Search Report of PCT application No. PCT/JP2019/005590 dated May 7, 2019.

\* cited by examiner

DETECTION APPARATUS, DETECTION SUBSTRATE, AND DETECTION METHOD

BACKGROUND

1. Technical Field

The present disclosure relates to a detection substrate having a metal microstructure (hereinafter referred to as metal nanostructure), and a detection apparatus and the like including the detection substrate. Metal nanostructures enhance raman scattered light and fluorescence generated in the vicinity thereof by the action of local surface plasmon resonance. In particular, the present disclosure relates to a device and the like that detect a detection object substance by surface enhanced fluorescence spectroscopy, which detects fluorescence of fluorescent-labeled antibodies that bind with the detection object substance.

2. Description of the Related Art

As an existing technique that detects protein, there is a technique that utilizes surface enhanced fluorescence. This technique provides a region that includes a metal nanostructure formed therein in a flow passage in which a solution is to be made to flow and immobilizes antibodies (hereinafter referred to as immobilized antibodies) that bind with a detection object substance on the metal nanostructure. When a sample solution containing the detection object substance and fluorescent-labeled antibodies (hereinafter referred to as labeled antibodies) is dropped into the flow passage, the detection object substance binding with the labeled antibodies is captured by the immobilized antibodies. When the captured detection object substance is irradiated with light having a wavelength that causes the metal nanostructure to generate local surface plasmon resonance, fluorescence generated in the labeled antibodies is enhanced and becomes surface enhanced fluorescence. The degree of the enhancement of the fluorescence by the local surface plasmon resonance is called an enhancement degree. The intensity of the surface enhanced fluorescence increases in accordance with an increase in the concentration of the detection object substance. The enhancement degree has approximately 1 to 3 digits (that is, 10 to 1000 times), and the surface enhanced fluorescence thus shows intensity that is higher than that of normal fluorescence by approximately 1 to 3 digits. Therefore, it is possible to detect a low-concentration detection object substance that is unmeasurable with normal fluorescence (refer to Japanese Unexamined Patent Application Publication No. 2010-19765).

SUMMARY

In the aforementioned technique, however, fluorescence is generated not only in the labeled antibodies binding with the detection object substance but also in the labeled antibodies not binding with the detection object, which degrades accuracy in detection of the detection object substance. Although the labeled antibodies not binding with the detection object substance are removable, such removing complicates operations and increases a detection time.

Thus, one non-limiting and exemplary embodiment of the present disclosure provides a detection apparatus and the like capable of suppressing, without removing labeled antibodies not binding with a detection object substance, detection accuracy from being degraded by the labeled antibodies.

In one general aspect, the techniques disclosed here feature a detection apparatus including: a substrate having a first major face and a second major face opposite to the first major face; a metal microstructure disposed on the first major face and on which a first specific binding substance having a property of binding with a detection object substance is immobilized, the metal microstructure generating a surface plasmon by being irradiated with excitation light; an introducer that introduces a second specific binding substance and a sample containing the detection object substance into the metal microstructure, the second specific binding substance having a property of binding with the detection object substance and being labeled with a fluorescent material; a light irradiator that irradiates the metal microstructure into which the second specific binding substance and the sample have been introduced with the excitation light from a side of the second major face of the substrate; and a detector that detects the detection object substance based on fluorescence generated from the fluorescent material in response to irradiation of the excitation light. The metal microstructure includes a light transmissive portion that transmits, to a side of the first major face, the excitation light emitted from the side of the second major face. The metal microstructure further includes a non-light transmissive portion having lower transparency to the excitation light than the light transmissive portion. The substrate has a property of transmitting the excitation light. The non-light transmissive portion is a region in the first major face covered with a metal film. The light transmissive portion is a region in the first major face not covered with the metal film or a region of the first major face covered with the metal film thinner than the metal film on the non-light transmissive portion.

It should be noted that general or specific aspects may be implemented as a system, a method, an integrated circuit, a computer program, or a computer-readable storage medium or may be implemented as any selective combination of a device, a system, a method, an integrated circuit, a computer program, and a storage medium. The computer-readable storage medium includes a nonvolatile storage medium, for example, a CD-ROM (compact disc-read only memory) or the like.

According to the present disclosure, it is possible to suppress, without removing labeled antibodies not binding with a detection object substance, detection accuracy from being degraded by the labeled antibodies. Additional benefits and advantages of the one aspect of the present disclosure will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Underlying Knowledge Forming Basis of the Present Disclosure

In surface enhanced fluorescence spectroscopy utilizing a metal nanostructure, immobilized antibodies immobilized on the metal nanostructure capture labeled antibodies via a detection object substance. Then, fluorescence generated in the labeled antibodies is enhanced by local surface plasmon resonance. The enhanced fluorescence, that is, surface enhanced fluorescence is detected, and the detection object substance is thereby detected. Detection of a detection object substance means measurement of the concentration of the detection object substance. Measurement of the concentration of a detection object substance includes, in addition to measurement of the absolute concentration of the detection object substance in a test solution, measurement of the relative concentration thereof in relation to a predetermined concentration.

As above, in a method that utilizes enhancement by local surface plasmon resonance generated in a metal nanostructure, excitation light for generating local surface plasmon resonance is emitted from a side of a face (hereinafter referred to as surface) along which the metal nanostructure and a test solution containing a detection object substance are in contact with each other.

Figure 1:
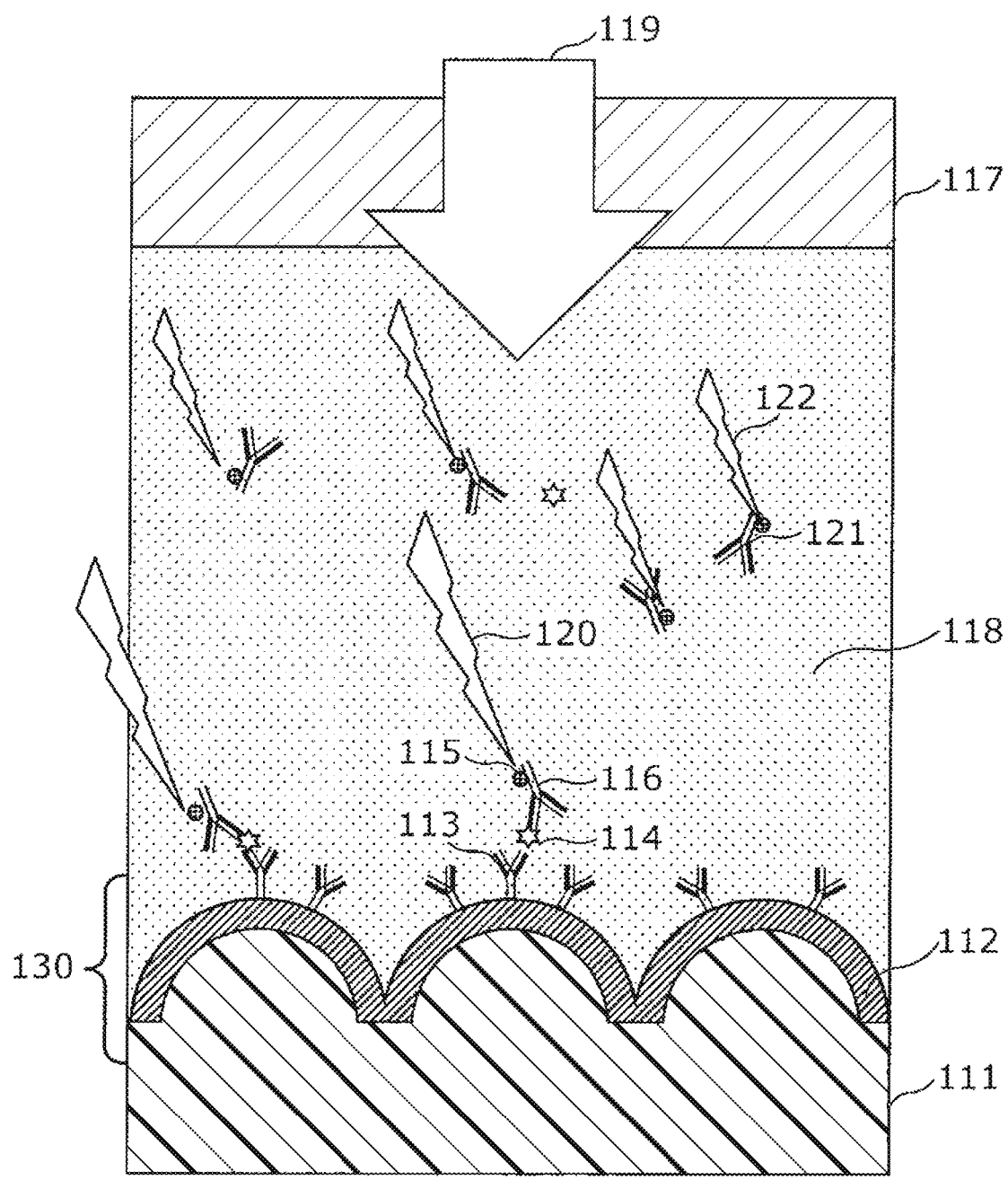
FIG. 1 illustrates surface enhanced fluorescence spectroscopy in underlying knowledge forming basis of the present disclosure.

FIG. 1 illustrates surface enhanced fluorescence spectroscopy in underlying knowledge forming basis of the present disclosure. In FIG. 1, a substrate 111 is formed of an olefin resin or the like and includes, on a surface thereof, semicircular projections each having a diameter of approximately 100 to 2000 nm. The surface of the substrate 111 is covered with a metal film 112 formed of metal, such as gold, silver, aluminum, or the like, and having a film thickness of approximately 30 to 1000 nm.

Being formed on the projections of the surface of the substrate 111, the metal film 112 forms a semicircular projection structure having a diameter of approximately 100 to 2000 nm, that is, a metal nanostructure 130. When the metal nanostructure 130 is irradiated with light having a specific wavelength, local surface plasmon resonance is generated.

Immobilized antibodies 113 are immobilized on the metal film 112. A detection object substance 114 binds with the immobilized antibodies 113. Labeled antibodies 116 are labeled with a fluorescent material 115. The labeled antibodies 116 binds with the detection object substance 114. In other words, the detection object substance 114 is held between the immobilized antibodies 113 and the labeled antibodies 116.

A transparent cover 117 is formed of glass, resin, or the like and holds a test solution 118 containing the detection object substance 114 between the transparent cover 117 and the substrate 111. The metal nanostructure 130 is irradiated with excitation light 119 through the transparent cover 117. The excitation light 119 has a wavelength capable of causing local surface plasmon resonance to be generated in the metal nanostructure 130 and exciting the fluorescent material 115.

In response to irradiation of the excitation light 119, the metal nanostructure 130 generates local surface plasmon resonance, and a fluorescence 120 is generated from the labeled antibodies 116 captured by the immobilized antibodies 113 via the detection object substance 114. The fluorescence 120 is enhanced by the local surface plasmon resonance. The enhanced fluorescence 120 exits to the outside by being transmitted through the transparent cover 117 and is detected by a photodetector (not illustrated).

The number of the labeled antibodies 116 captured by the immobilized antibodies 113 increases in accordance with an increase of the detection object substance 114. The intensity of the fluorescence 120 detected by the photodetector is proportional to the number of the labeled antibodies 116 captured by the immobilized antibodies 113. It is thus possible to measure the concentration of the detection object substance 114 by measuring the intensity of the fluorescence 120. Here, the labeled antibodies 116 binding with the detection object substance 114 are referred to as component B.

Labeled antibodies 121 not binding with the detection object substance 114 are also irradiated with the excitation light 119, and thus, fluorescence 122 is generated from the labeled antibodies 121. Here, the free labeled antibodies 121 not binding with the detection object substance 114 are referred to as component F. The fluorescence 122 that is generated from the component F does not reflect the concentration of the detection object substance 114. The fluorescence 122 generated from the component F is a mere noise component and interferes measurement of the fluorescence 120 generated from the component B, which degrades measurement accuracy.

For example, when the fluorescence 122 generated from the component F is strong, the photodetector may be saturated and may become incapable of performing measurement. When the intensity of the excitation light 119 is reduced to prevent such saturation, measurement accuracy, in particular, when the concentration of the detection object substance 114 is low is degraded.

Moreover, due to the test solution 118 being irradiated at the entirety thereof with the excitation light 119, scattered light and fluorescence of substances coexisting in the test solution 118 become noise by entering the photodetector. When the test solution 118 is a solution collected from environment or a living body, the test solution 118 highly likely contains a large amount of coexisting substances mixed therein; therefore, degradation of measurement accuracy caused by scattered light and fluorescence from the coexisting substances is considerable.

To eliminate interference of the component F with respect to the detection of the component B, the periphery of the metal nanostructure 130 may be cleansed after a reaction in which the labeled antibodies 116 are captured by the immobilized antibodies 113 via the detection object substance 114 is completed, and the labeled antibodies 121, which are the component F, not binding with the detection object substance 114 may be removed (BF separation). In this case, it is possible to improve accuracy in the measurement of the concentration of the detection object substance 114 by performing irradiation of the excitation light 119 after the cleansing.

Such BF separation, however, complicates a measurement operation. Moreover, the BF separation cannot be started until the reaction in which the labeled antibodies 116 are captured by the immobilized antibodies 113 via the detection object substance 114 is completed, which impedes a reduction in measurement time. Further, there is a possibility that cleansing the periphery of the metal nanostructure 130 removes, in addition to the labeled antibodies 121 of the component F, the labeled antibodies 116 of the component B captured by the immobilized antibodies 113.

As a method that does not use the BF separation, as described in Japanese Unexamined Patent Application Publication No. 2008-216046, there is a method that utilizes a back-side irradiation system in which light is emitted from the back side of a substrate. In this method, evanescent waves are induced by emitting the light from the back surface side of the substrate. In response to labeled antibodies captured by immobilized antibodies being irradiated with the evanescent waves, fluorescence is generated from the labeled antibodies. In this method, only a region away by a few hundred nanometers from the substrate surface on which antibodies are immobilized is irradiated with the evanescent waves. Therefore, it is possible to reduce the amount of light that the component F or coexisting substances are irradiated with, compared with when the light is emitted from the surface side of the substrate as is in existing methods.

However, considering that the labeled antibodies captured by the immobilized antibodies are positioned away from the substrate surface by approximately 10 nm, an irradiation region of the evanescent waves is excessive, and an effect of reducing fluorescence generated from the component F is limited. Furthermore, to induce the evanescent waves, it is required to strictly adjust the angle of incident of the light onto the substrate, which complicates an optical system.

As above, in the method utilizing the BF separation, not only the measurement operation becomes complicated, but also a reduction in measurement time is impeded. In the method in Japanese Unexamined Patent Application Publication No. 2008-216046 utilizing evanescent waves, limitation of the irradiation region is insufficient, and a more complicated optical system is required.

Then, a detection apparatus according to one aspect of the present disclosure includes: a substrate having a first major face and a second major face opposite to the first major face; a metal microstructure disposed on the first major face and on which a first specific binding substance having a property of binding with a detection object substance is immobilized, the metal microstructure generating a surface plasmon by being irradiated with excitation light; an introducer that introduces a second specific binding substance and a sample containing the detection object substance into the metal microstructure, the second specific binding substance having a property of binding with the detection object substance and being labeled with a fluorescent material; a light irradiator that irradiates the metal microstructure into which the second specific binding substance and the sample have been introduced with the excitation light from a side of the second major face of the substrate; and a detector that detects the detection object substance based on fluorescence generated from the fluorescent material in response to irradiation of the excitation light. The metal microstructure includes a light transmissive portion that transmits, to a side of the first major face, the excitation light emitted from the side of the second major face.

According to this, the metal microstructure includes the light transmissive portion that transmits, to the side of the first major face of the substrate, excitation light emitted from the side of the second major face of the substrate. Consequently, it is possible by using excitation light emitted from the side of the second major face of the substrate, without using a complicated optical system, to (i) cause a surface plasmon to be generated in the metal microstructure, (ii) cause fluorescence to be generated from the second specific binding substance captured by the first specific binding substance, and (iii) enhance the fluorescence by the surface plasmon. Therefore, it is possible to enhance, more than when excitation light is emitted from the side of the first major face, fluorescence (signal light) generated in the second specific binding substance captured by the first specific binding substance while limiting the irradiation range of the excitation light in the sample to be in the vicinity of the metal microstructure. As a result, the S/N ratio of the signal light relative to noise light generated in a portion other than the portion in the vicinity of the metal microstructure can be increased, which enables an improvement in accuracy in detection of the detection object substance. Moreover, it is also possible to omit a removal operation (that is, BF separation) of the second specific binding substance that is not captured by the first specific binding substance because fluorescence generated in the second specific binding substance (that is, the second specific binding substance not captured by the first specific binding substance) present in a location relatively away from the metal microstructure can be reduced.

In addition, in the detection apparatus according to the one aspect of the present disclosure, the metal microstructure may further include a non-light transmissive portion having lower transparency to the excitation light than the light transmissive portion, the substrate may have a property of transmitting the excitation light, the non-light transmissive portion may be a region in the first major face covered with a metal film, and the light transmissive portion may be a region in the first major face not covered with the metal film or may be a region of the first major face covered with the metal film thinner than the metal film on the non-light transmissive portion.

According to this, the metal microstructure can include, in addition to the light transmissive portion, the non-light transmissive portion covered with the metal film. Therefore, it is possible to introduce the excitation light to the side of the first major face of the substrate by the light transmissive portion, and it is possible to generate a surface plasmon by the non-light transmissive portion. In other words, transmission of the excitation light and control of the surface plasmon can be performed by the metal film, which can increase ease of manufacture of the metal microstructure for improving accuracy in detection of the detection object substance.

Moreover, in the detection apparatus according to the one aspect of the present disclosure, the metal microstructure may include projections, and the light transmissive portion may be regions in respective side surfaces of the projections.

According to this, it is possible to provide the light transmissive portion on each of the side surfaces of the projections. Therefore, it is possible to form the light transmissive portion and the non-light transmissive portion by forming the metal film on the upper surfaces of the projections of the substrate and on the bottom surfaces of grooves between the projections by using, for example, a film forming method, such as electron beam deposition, which enables the metal microstructure to be manufactured relatively easily. Moreover, it is possible to limit the irradiation range of the excitation light in the sample to be closer to the metal microstructure, and it is thus possible to further improve accuracy in detection of the detection object substance.

In addition, in the detection apparatus according to the one aspect of the present disclosure, the metal microstructure may have a line-and-space structure, and each of the projections may have a linear shape.

According to this, it is possible to employ the line-and-space structure in the metal microstructure. The line-and-space structure is a relatively simple structure and thus can reduce difficulty in designing the metal microstructure for improving accuracy in detection of the detection object structure.

In addition, in the detection apparatus according to the one aspect of the present disclosure, the metal film may be formed of silver.

According to this, it is possible to use silver as the metal film.

In addition, in the detection apparatus according to the one aspect of the present disclosure, the second specific binding substance may be bound with metal colloid particles.

According to this, it is possible to bind the metal colloid particles with the second specific binding substance. Therefore, a surface plasmon can be also generated between the metal microstructure and the metal colloid particles, and the fluorescence can be further enhanced. In particular, an effect of enhancing the fluorescence generated in the second specific binding substance captured by the first specific binding substance can be improved because the closer the metal colloid particles to the metal microstructure, the stronger surface plasmon can be generated.

In addition, in the detection apparatus according to the one aspect of the present disclosure, the metal colloid particles may be gold colloid particles.

According to this, it is possible to use gold colloid particles as the metal colloid particles.

A detection substrate according to one aspect of the present disclosure is a detection substrate for detecting a detection object substance and includes a substrate having a first major face and a second major face opposite to the first major face; and a metal microstructure disposed on the first major face of the substrate and on which a first specific binding substance having a property of binding with the detection object substance is immobilized, the metal microstructure generating a surface plasmon by being irradiated with excitation light. The metal microstructure includes a light transmissive portion that transmits, to a side of the first major face, the excitation light emitted from a side of the second major face.

Detecting the detection object substance by using the detection substrate can obtain the same effect as that of the aforementioned detection apparatus.

A detection method according to one aspect of the present disclosure includes: introducing a second specific binding substance having a property of binding with a detection object substance, the second specific binding substance being labeled with a fluorescent material, and a sample containing the detection object substance into a metal microstructure (i) that is disposed on a first major face of a substrate, (ii) that generates a surface plasmon by being irradiated with excitation light, and (iii) on which a first specific binding substance having a property of binding with the detection object substance is immobilized; irradiating the metal microstructure into which the second specific binding substance and the sample have been introduced with the excitation light from a side of a second major face opposite to the first major face of the substrate; and detecting the detection object substance based on fluorescence generated from the fluorescent material in response to irradiation of the excitation light. The metal microstructure includes a light transmissive portion that transmits, to a side of the first major face, the excitation light emitted from the side of the second major face.

According to this, it is possible to obtain the same effect as that of the aforementioned detection apparatus.

It should be noted that these general or specific aspects may be implemented as a system, an integrated circuit, a computer program, or a computer-readable storage medium, such as a CD-ROM, or may be implemented as any selective combination of a system, an integrated circuit, a computer program, and a storage medium.

Embodiments

Hereinafter, embodiments will be specifically described with reference to the drawings.

Note that the embodiments described below each indicate a general or specific example. The numerical values, shapes, materials, constituent elements, arranged positions and connection forms of the constituent elements, steps, the order of the steps, and the like indicated in the following embodiments are each presented as an example and do not intend to limit the claims. Among the constituent elements in the following embodiments, constituent elements that are not described in an independent claim indicating a most generic concept are described as selective constituent elements. Each of the drawings is not necessarily strictly illustrated. In the drawings, constituents substantially identical to each other are given identical signs, and duplicate description thereof will be omitted or simplified.

Configuration of Detection Apparatus

Figure 2:
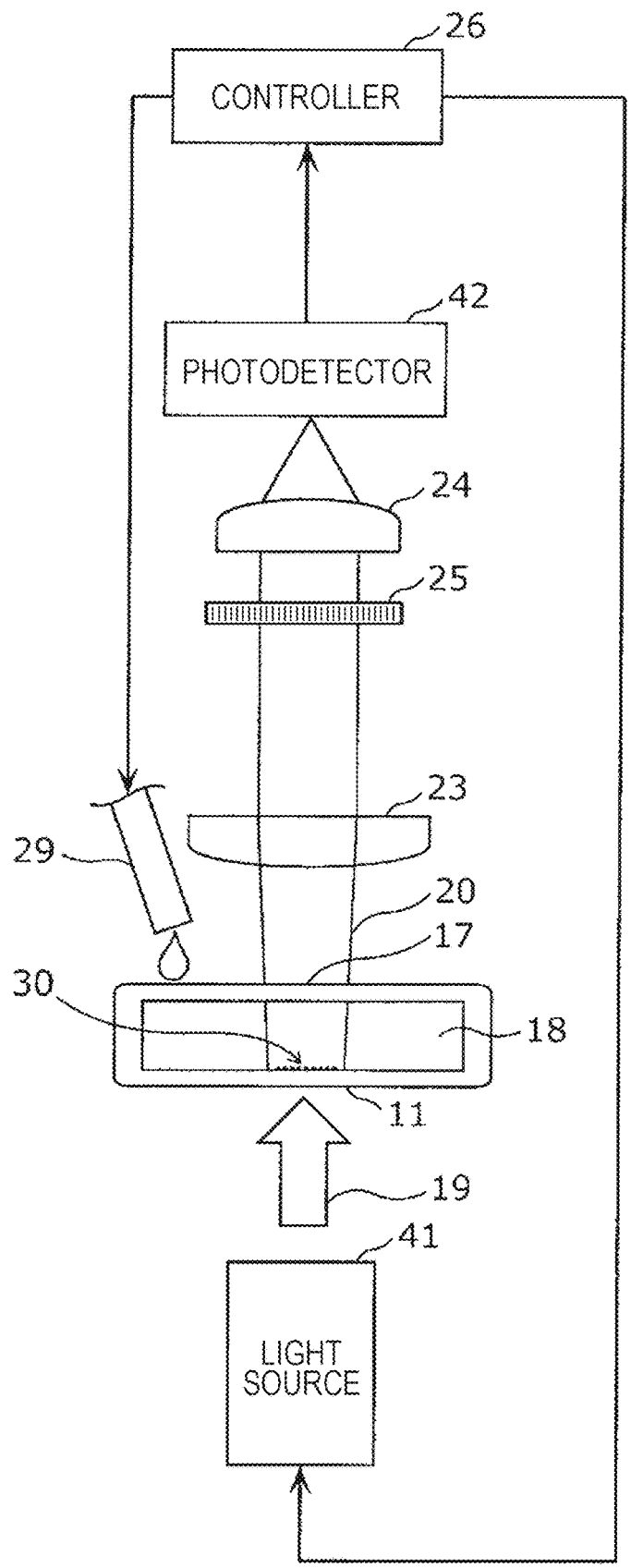
FIG. 2 is a block diagram of a detection apparatus according to an embodiment.

FIG. 2 is a block diagram of a detection apparatus according to an embodiment.

As illustrated in FIG. 2, the detection apparatus according to the present embodiment includes a substrate 11, a metal nanostructure 30, an introducer 29, a light source 41, a photodetector 42, and a controller 26. In the present embodiment, the detection apparatus further includes a transparent cover 17, lenses 23 and 24, and a long-path filter 25.

The substrate 11 has a first major face (hereinafter referred to as surface) and a second major face (hereinafter referred to as back surface) opposite to the first major face. The substrate 11 has a property of transmitting excitation light 19. A test solution 18 is held between the substrate 11 and the transparent cover 17.

The metal nanostructure 30 is formed by covering at least a portion of the surface of the substrate 11 with a metal film. Immobilized antibodies having a property of binding with a detection object substance are immobilized on the metal nanostructure 30. The detection object substance is, for example, a pathogen-derived molecule. As an example of the pathogen-derived molecule, a nuclear protein (NP) of an influenza virus is presented. The immobilized antibodies are an example of the first specific binding substance and are, for example, IgG antibodies or VHH antibodies. When the immobilized antibodies have a binding capacity with respect to the metal nanostructure 30, direct immobilization thereof is possible. When the immobilized antibodies do not have the binding capacity, the immobilized antibodies can be indirectly immobilized via a linker material, such as an organic molecule.

A surface plasmon is generated by irradiating the metal nanostructure 30 with excitation light having a specific wavelength. The metal nanostructure 30 includes a light transmissive portion that transmits, to the surface side of the substrate 11, the excitation light 19 emitted from the back surface side of the substrate 11. Details of the metal nanostructure 30 will be described later by using FIG. 3 to FIG. 5.

The introducer 29 introduces, into the metal nanostructure 30, labeled antibodies and the test solution 18 containing a detection object substance. The labeled antibodies are an example of the second specific binding substance. The labeled antibodies are labeled with a fluorescent material and have a property of binding with the detection object substance. Specifically, the labeled antibodies are, for example, IgG antibodies or VHH antibodies. The test solution 18 is sometimes referred to as a sample.

Specifically, the introducer 29 drops the test solution 18 into, for example, a through hole disposed in the transparent cover 17. More specifically, the introducer 29 may include, for example, a pump (not illustrated) and a valve (not illustrated). In this case, the introducer 29 may introduce the test solution 18 into the metal nanostructure 30 by actuating the pump by opening the valve.

The light source 41 is an example of a light irradiator and emits the excitation light 19, which is substantially parallel light, from the back surface side of the substrate 11. The excitation light 19 emitted from the back surface side of the substrate 11 is transmitted to the surface side of the substrate 11 through the light transmissive portion of the metal nanostructure 30 and irradiates the metal nanostructure 30.

The labeled antibodies captured by the immobilized antibodies are irradiated with the excitation light 19 and emit fluorescence 20 from the fluorescent material. The fluorescence 20 generated in the labeled antibodies is enhanced by local surface plasmon resonance. The enhanced fluorescence 20 is transmitted through the transparent cover 17 and guided into the photodetector 42 through the lens 23, the long-path filter 25, and the lens 24. The long-path filter 25 reduces a wavelength component of the excitation light 19 and transmits a wavelength component of the fluorescence 20.

The photodetector 42 separates the fluorescence 20 and detects a spectrum. The photodetector 42 outputs spectrum data of the fluorescence 20 as an output signal to the controller 26.

The controller 26 includes a processor and a memory and is realized by a software program stored in the memory being executed by the processor. The controller 26 may be constituted by a dedicated electronic circuit. The controller 26 analyzes the spectrum data, which is the output signal of the photodetector 42, of the fluorescence 20 and calculates the concentration of the detection object substance. In addition, the controller 26 controls the light source 41 and the introducer 29.

A set of the photodetector 42 and the controller 26 is an example of a detector and detects the detection object substance on the basis of fluorescence generated from the fluorescent material in response to irradiation with the excitation light 19.

Metal Nanostructure

Figure 3:
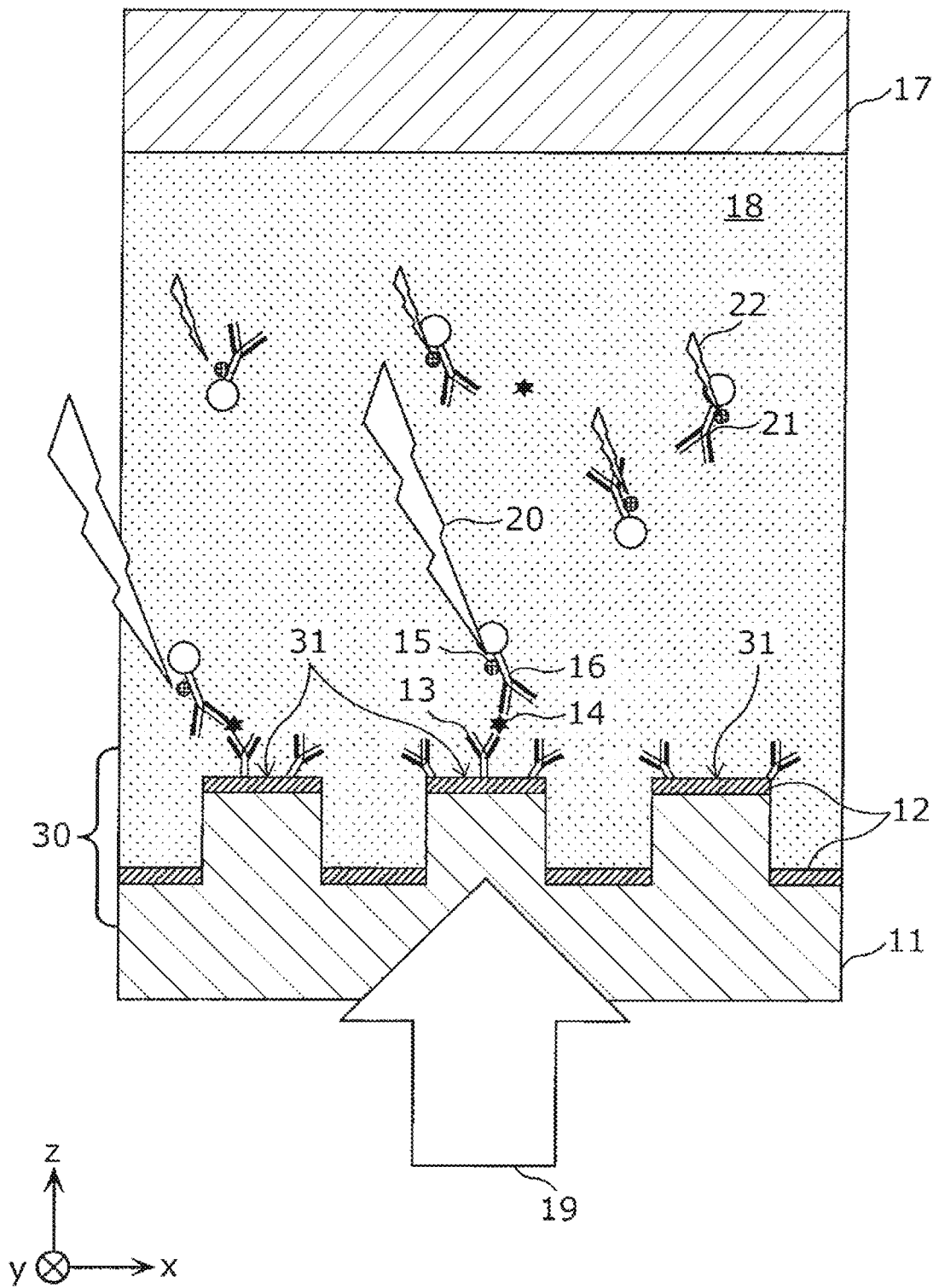
FIG. 3 is a sectional view of a metal nanostructure according to an embodiment.
Figure 4:
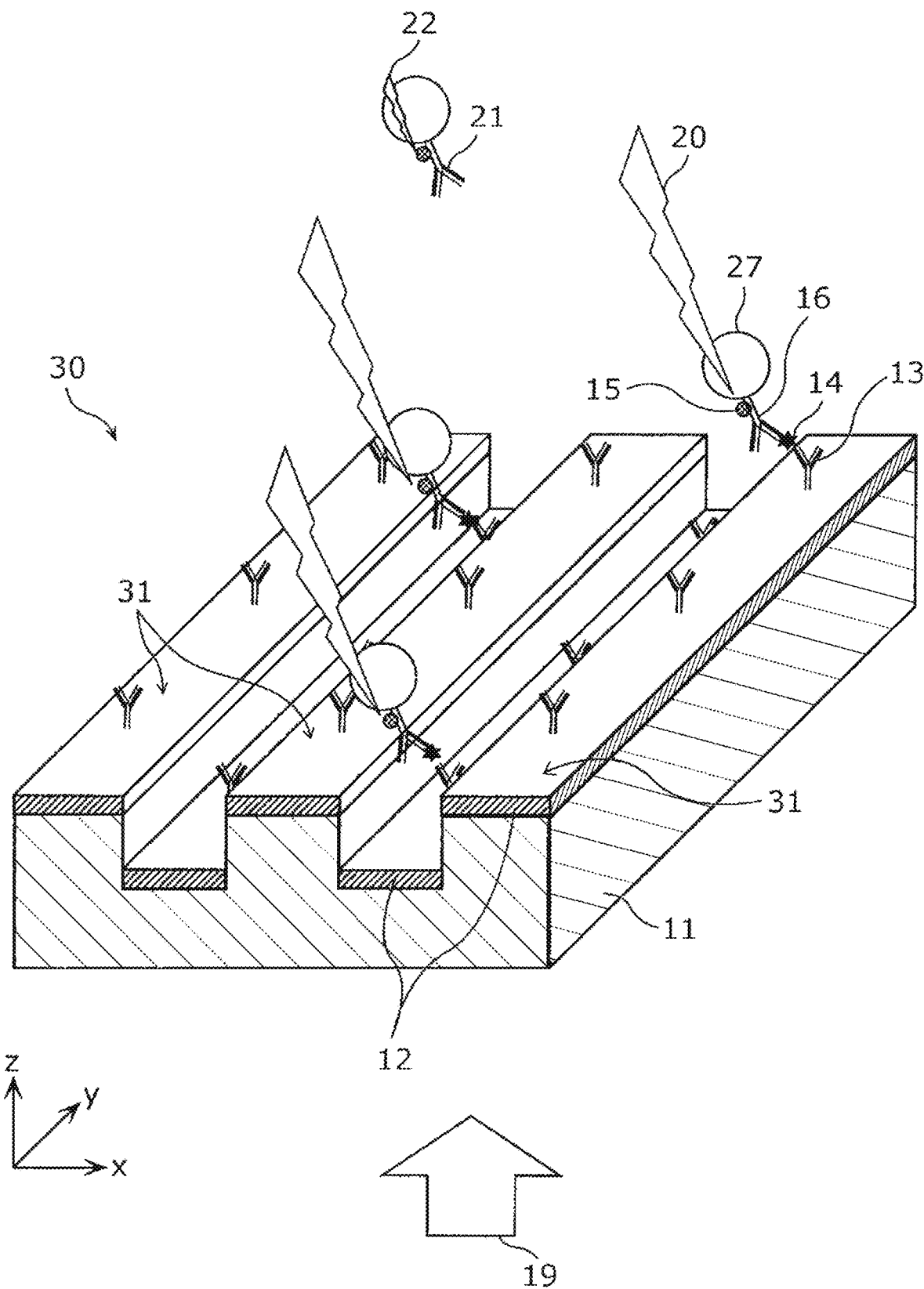
FIG. 4 is a perspective view of a metal nanostructure according to an embodiment.
Figure 5:
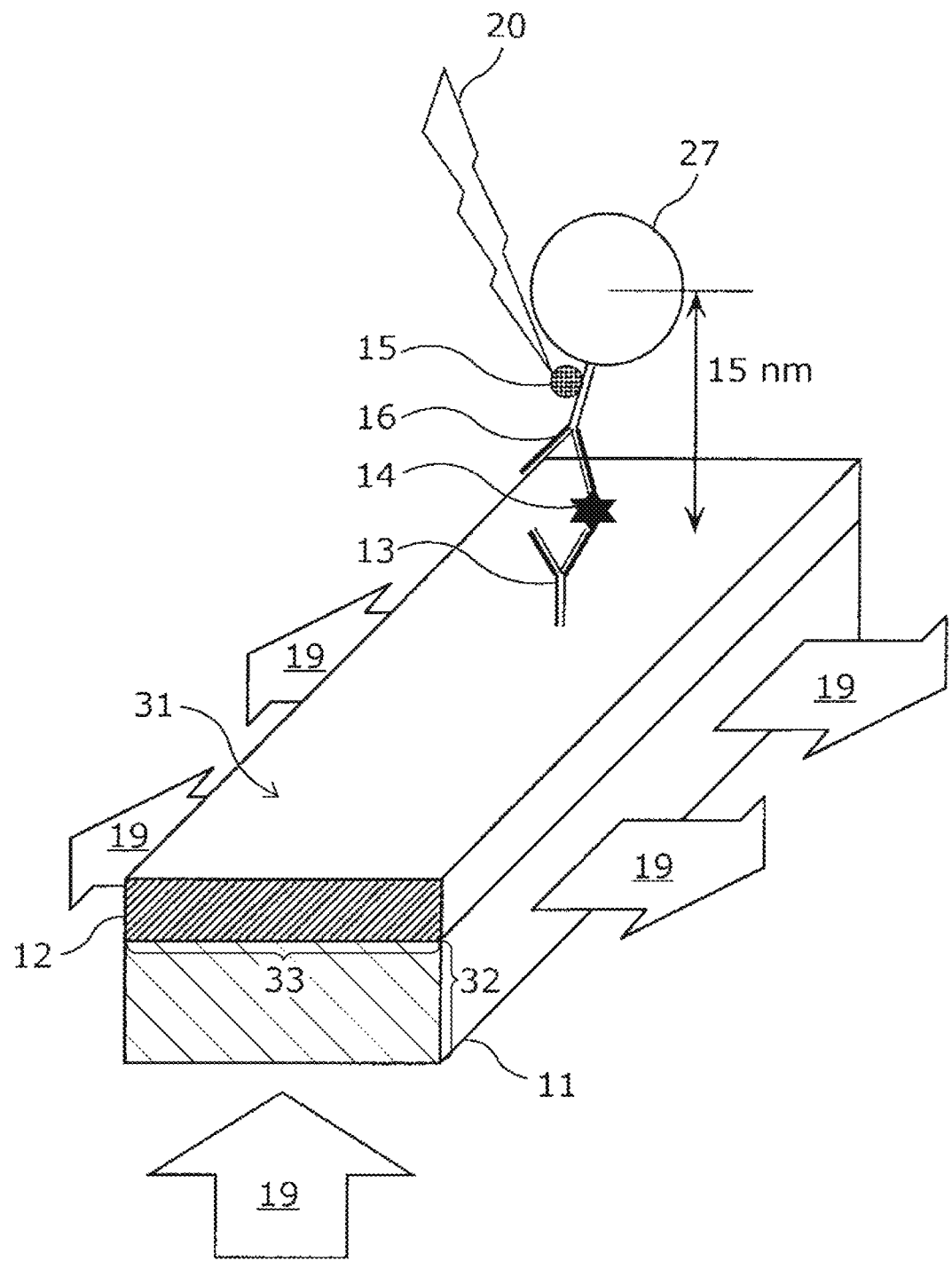
FIG. 5 is an enlarged perspective view of a projection of the metal nanostructure according to an embodiment.

Next, details of the metal nanostructure 30 will be specifically described with reference to FIG. 3 to FIG. 5. FIG. 3 is a sectional view of the metal nanostructure 30 in an embodiment. FIG. 4 is a perspective view of the metal nanostructure 30 according to the embodiment. FIG. 5 is an enlarged perspective view of a projection 31 of the metal nanostructure 30 according to the embodiment.

The substrate 11 is made of an olefin resin or the like that transmits the excitation light 19. On the surface of the substrate 11, linear projections each having a width of approximately 10 to 2000 nm and a height of approximately 10 to 4000 nm are disposed at intervals substantially identical to the width of the linear projections. The projections of the substrate 11 are formed by, for example, a nanoimprint method.

A metal film 12 is formed of, for example, metal, such as gold, silver, aluminum, or the like. The film thickness of the metal film 12 is approximately 10 to 1000 nm. The metal film 12 is formed on the surface of the substrate 11 by, for example, electronic beam deposition. As a result, the substrate 11 and the metal film 12 form the metal nanostructure 30 including the linear projections 31 each having a width of approximately 10 to 2000 nm and a thickness of approximately 10 to 1000 nm. In other words, the substrate 11 and the metal film 12 form the metal nanostructure 30 that has a so-called line-and-space structure. The line-and-space structure has anisotropy, in which the structure in a line direction (y direction) and the structure in a direction (x direction) orthogonal to the line direction differ from each other.

As illustrated in FIG. 5, the metal nanostructure 30 includes a light transmissive portion 32 and a non-light transmissive portion 33.

The light transmissive portion 32 transmits, to the surface side of the substrate 11, the excitation light 19 emitted from the back surface side of the substrate 11. Specifically, the light transmissive portion 32 is a region in the surface of the substrate 11 not covered with the metal film 12. More specifically, the light transmissive portion 32 is a region in a side surface (yz face) of each of the linear projections 31.

The non-light transmissive portion 33 is a region in the surface of the substrate 11 having lower transparency to the excitation light 19 than the light transmissive portion 32 and is a region in the surface of the substrate 11 covered with the metal film 12. In the present embodiment, the non-light transmissive portion 33 is a region in the upper surface (xy face) of each of the linear projections 31 and in the bottom surface (xy face) of each of grooves between the projections 31. Immobilized antibodies 13 are immobilized on the non-light transmissive portion 33.

The metal nanostructure 30 generates local surface plasmon resonance when being irradiated with light having a specific wavelength in a specific polarization direction. The local surface plasmon resonance enhances fluorescence generated in the periphery of the metal nanostructure 30. A resonance wavelength and an enhancement degree with which local surface plasmon resonance is generated depend on the size, the metal type, and the metal surface roughness of the metal nanostructure 30. For example, in the metal nanostructure 30 of the present embodiment, the resonance wavelength and the enhancement degree for the local surface plasmon resonance depend on the width, the height, and the intervals of the linear projections 31 illustrated in FIG. 3 to FIG. 5 and the film thickness and the surface roughness of the metal film 12.

The immobilized antibodies 13 are immobilized on the metal film 12. A detection object substance 14 binds with the immobilized antibodies 13. Labeled antibodies 16 are labeled with a fluorescent material 15. The labeled antibodies 16 further bind with gold colloid particles (hereinafter referred to as gold colloid 27) each having a diameter of approximately 10 nm. As illustrated in FIG. 5, the gold colloid 27 is immobilized on the metal film 12 via the labeled antibodies 16, the detection object substance 14, and the immobilized antibodies 13. The distance between the gold colloid 27 and the metal film 12 is approximately 15 nm.

When the excitation light 19 is emitted from the back surface side of the substrate 11, the excitation light 19 reaches the surface side of the substrate 11 through the light transmissive portion 32 and irradiates the metal nanostructure 30. As a result, local surface plasmon resonance is generated in the metal nanostructure 30.

Further, in FIG. 3 to FIG. 5, local surface plasmon resonance is also generated in the gold colloid 27 due to diffraction of the excitation light 19 that exits from the side surfaces (yz faces) of the linear projections 31 and light radiation from the local surface plasmon resonance generated in the metal film 12. The fluorescence 20 from the fluorescent material 15 is further enhanced by the action of the local surface plasmon resonance generated in these two locations.

The excitation light 19 is not necessarily a substantially parallel light as long as having a wavelength that causes local surface plasmon resonance to be generated. The excitation light 19 may be light that is made incident obliquely like diffused light. Thus, it is possible to emit the excitation light 19 by a simple optical system.

Incidentally, most of labeled antibodies 21 not captured by the immobilized antibodies 13 are present in a region relatively away from the metal nanostructure 30 and in which the degree of electrical field enhancement is low. Thus, fluorescence 22 from the labeled antibodies 21, which are the component F, is mostly not enhanced, and the intensity of the fluorescence 22 from the labeled antibodies 21, which are the component F, can be suppressed.

Operation of Detection Apparatus

Figure 6:
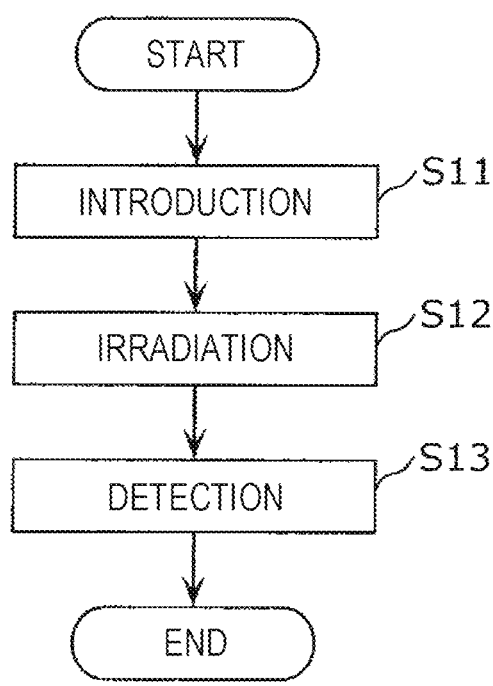
FIG. 6 is a flowchart of a detection method according to an embodiment.

Next, an operation of the detection apparatus configured as described above will be described with reference to FIG. 6. FIG. 6 is a flowchart of a detection method according to an embodiment.

First, the controller 26 introduces the labeled antibodies 16 and the test solution 18 into the metal nanostructure 30 by using the introducer 29 (S11). Consequently, the detection object substance 14 contained in the test solution 18 binds with the immobilized antibodies 13 and the labeled antibodies 16 (antigen-antibody reaction). Here, a so-called sandwich method, which forms a complex in which the detection object substance 14 is sandwiched between the immobilized antibodies 13 and the labeled antibodies 16, is employed.

The binding capacity of the immobilized antibodies 13 with respect to the detection object substance 14 may be adjustable. The binding capacity of the labeled antibodies 16 with respect to the detection object substance 14 may be adjustable.

Next, the controller 26 emits the excitation light 19 from the back surface side of the substrate 11 by using the light source 41 (S12). Consequently, the metal nanostructure 30, the gold colloid 27, and the labeled antibodies 16 are irradiated with the excitation light 19 from the surface side of the substrate 11 through the light transmissive portion 32 of the metal nanostructure 30. As a result, the fluorescence 20 is emitted from the fluorescent material 15 of the labeled antibodies 16, and local surface plasmon resonance is generated in the vicinity of the metal nanostructure 30 and the gold colloid 27. The fluorescence 20 emitted from the labeled antibodies 16 is enhanced by the local surface plasmon resonance.

Lastly, the controller 26 detects the enhanced fluorescence 20 by using the photodetector 42, thereby detecting the detection object substance 14 (S13).

Effects

As above, in the detection apparatus according to the present embodiment, the metal nanostructure 30 includes the light transmissive portion 32 that transmits, to the surface side of the substrate 11, the excitation light 19 emitted from the back surface side of the substrate 11. Consequently, it is possible, without using a complicated optical system, by using the excitation light 19 emitted from the back surface side of the substrate 11 to (i) cause a surface plasmon to be generated in the metal nanostructure 30, (ii) cause fluorescence to be generated from the labeled antibodies 16 captured by the immobilized antibodies 13, and (iii) enhance the fluorescence by the surface plasmon. Therefore, it is possible to enhance, more than when the excitation light 19 is emitted from the surface side of the substrate 11, the fluorescence 20 (signal light) generated in the labeled antibodies 16 captured by the immobilized antibodies 13 while limiting the irradiation range of the excitation light 19 in the test solution 18 to be in the vicinity of the metal nanostructure 30. As a result, it is possible to increase the S/N ratio of the signal light in relation to noise light generated in a portion other than the portion in the vicinity of the metal nanostructure 30, which enables an improvement in accuracy in detection of the detection object substance 14. Moreover, it is possible to reduce the fluorescence 22 generated in the labeled antibodies 21 (that is, the labeled antibodies 21 not captured by the immobilized antibodies 13) present in a location relatively away from the metal nanostructure 30. Therefore, it is also possible to omit the removal operation (that is, BF separation) of the labeled antibodies 21 not captured by the immobilized antibodies 13.

In addition, in the detection apparatus according to the present embodiment, the metal nanostructure 30 can include, in addition to the light transmissive portion 32, the non-light transmissive portion 33 covered with the metal film 12. Therefore, it is possible to guide the excitation light 19 to the surface side of the substrate 11 by the light transmissive portion 32 and to generate a surface plasmon by the non-light transmissive portion 33. In other words, transmission of the excitation light 19 and control of the surface plasmon can be performed by the metal film 12, which enables an increase in ease of manufacture of the metal nanostructure 30 for improving accuracy in detection of the detection object substance 14.

In addition, in the detection apparatus according to the present embodiment, the light transmissive portion 32 can be provided in a side surface of each of the projections 31. Therefore, the light transmissive portion 32 and the non-light transmissive portion 33 can be formed by forming the metal film 12 on the upper surfaces of the projections of the substrate 11 and the bottom surfaces of the grooves between the projections by using, for example, a film forming method, such as electron beam deposition, which enables the metal nanostructure 30 to be manufactured relatively easily. Moreover, it is possible to limit the irradiation range of the excitation light 19 in the test solution 18 to be closer to the metal nanostructure 30, which enables a further improvement in accuracy in detection of the detection object substance.

In addition, in the detection apparatus according to the present embodiment, the line-and-space structure can be employed in the metal nanostructure 30. The line-and-space structure is a relatively simple structure and thus can reduce difficulty in designing the metal nanostructure 30 for improving accuracy in detection of the detection object substance 14.

In addition, in the detection apparatus according to the present embodiment, it is possible to bind the gold colloid 27 with the labeled antibodies 16. Therefore, it is possible to cause a surface plasmon to be also generated between the metal nanostructure 30 and the gold colloid 27, which enables fluorescence to be further enhanced. In particular, the closer the gold colloid 27 to the metal nanostructure 30, the stronger surface plasmon can be generated, and it is thus possible to improve the effect of enhancing the fluorescence generated in the labeled antibodies 16 captured by the immobilized antibodies 13.

As described above, by irradiating the metal nanostructure 30 including the light transmissive portion 32 in the side surfaces (yz faces) of the linear projections 31 with the excitation light 19 from the back surface side, it is possible to enhance and detect the fluorescence of the component B while suppressing generation of the fluorescence of the component F. It is thus possible to realize highly accurate measurement that requires no BF separation with a simple optical system.

EXAMPLE

Figure 7:
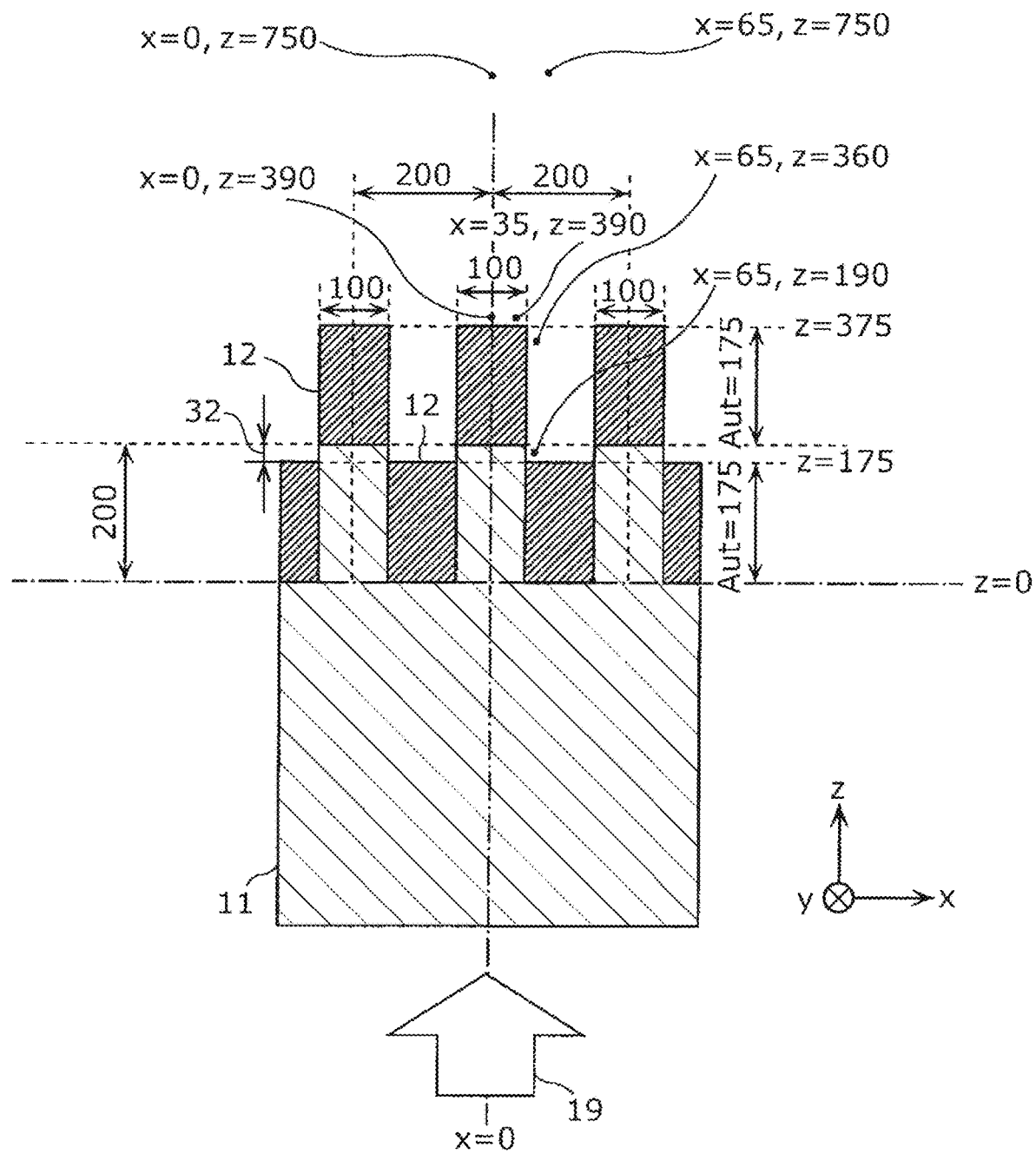
FIG. 7 is a sectional view of a metal nanostructure according to an example.

A result of simulation of the metal nanostructure will be described as an example of the present embodiment with reference to FIG. 7 to FIG. 10. FIG. 7 is a sectional view of a metal nanostructure according to an example.

In the simulation model of the present example, an olefin film was used as the substrate 11. On the olefin film, linear projections in which line width=100 nm, line height=200 nm, and line interval (pitch)=200 nm were formed. A metal nanostructure was formed on the substrate 11 by depositing silver, as the metal film 12, of a thickness of 175 nm. As a result, in the metal nanostructure, the linear light transmissive portions 32 with a width of Z=175 to 200 nm were formed on side surfaces (yz faces) of the linear projections.

The gold colloid 27 is positioned away from the metal film 12 by approximately 15 nm when the gold colloid is immobilized on the metal film 12 via a detection object. Therefore, in this simulation model, gold colloid was disposed in the following locations away from the surface of the metal film 12 by 15 nm, as illustrated in FIG. 7.
(1) x=65 nm, z=190 nm
(2) x=65 nm, z=360 nm
(3) x=35 nm, z=390 nm
(4) x=0 nm, z=390 nm
(5) x=−65 nm, z=190 nm (not illustrated)
(6) x=−65 nm, z=360 nm (not illustrated)
(7) x=−35 nm, z=390 nm (not illustrated)

The gold colloid 27 binding with the labeled antibodies 16 of the component B was modeled by the above gold colloid.

In addition, in this simulation model, gold colloid was also disposed in the following locations, as illustrated in FIG. 7.
(8) x=65 nm, z=750 nm
(9) x=0 nm, z=750 nm
(10) x=−65 nm, z=750 nm (not illustrated)

The gold colloid 27 binding with the labeled antibodies 21 of the component F was modeled by the above gold colloid.

Figure 8:
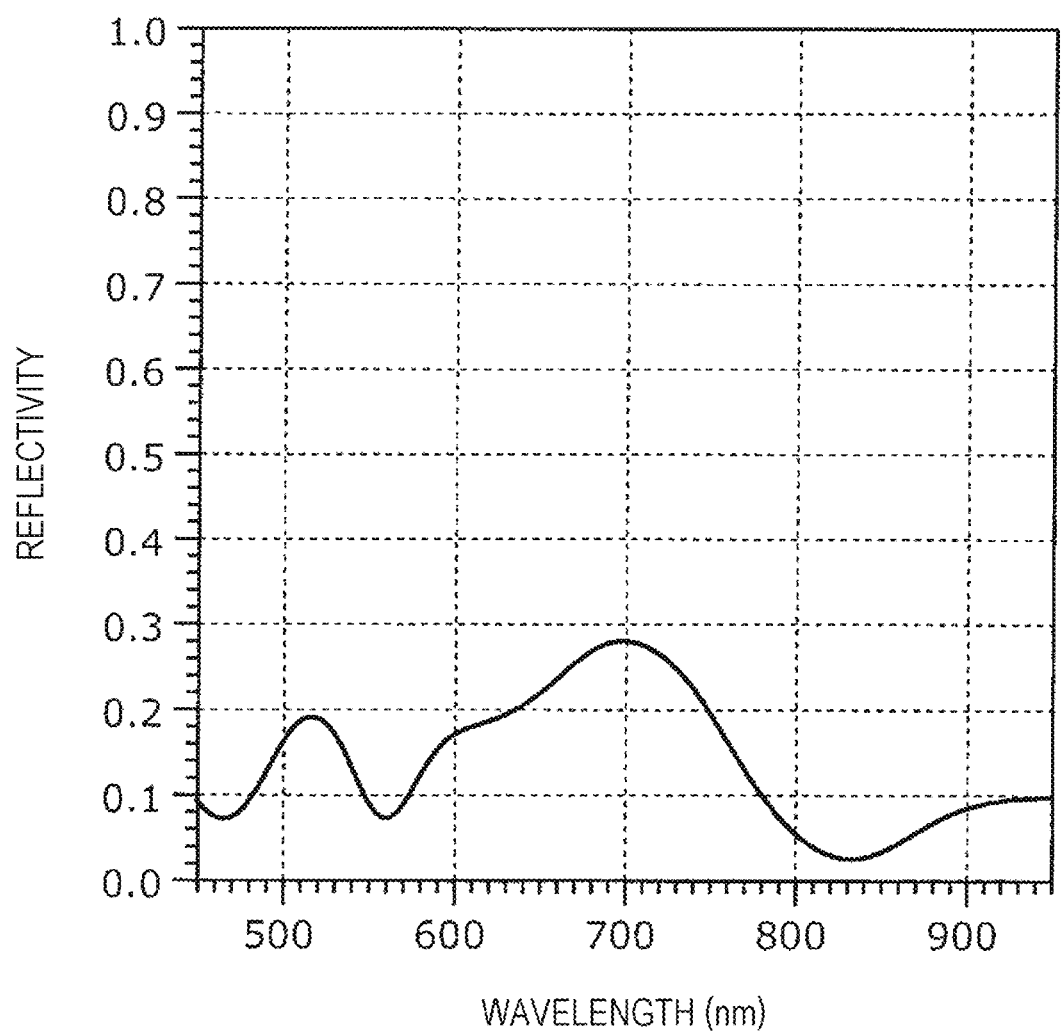
FIG. 8 is a graph of a reflection spectrum of a metal nanostructure according to an example.
Figure 9:
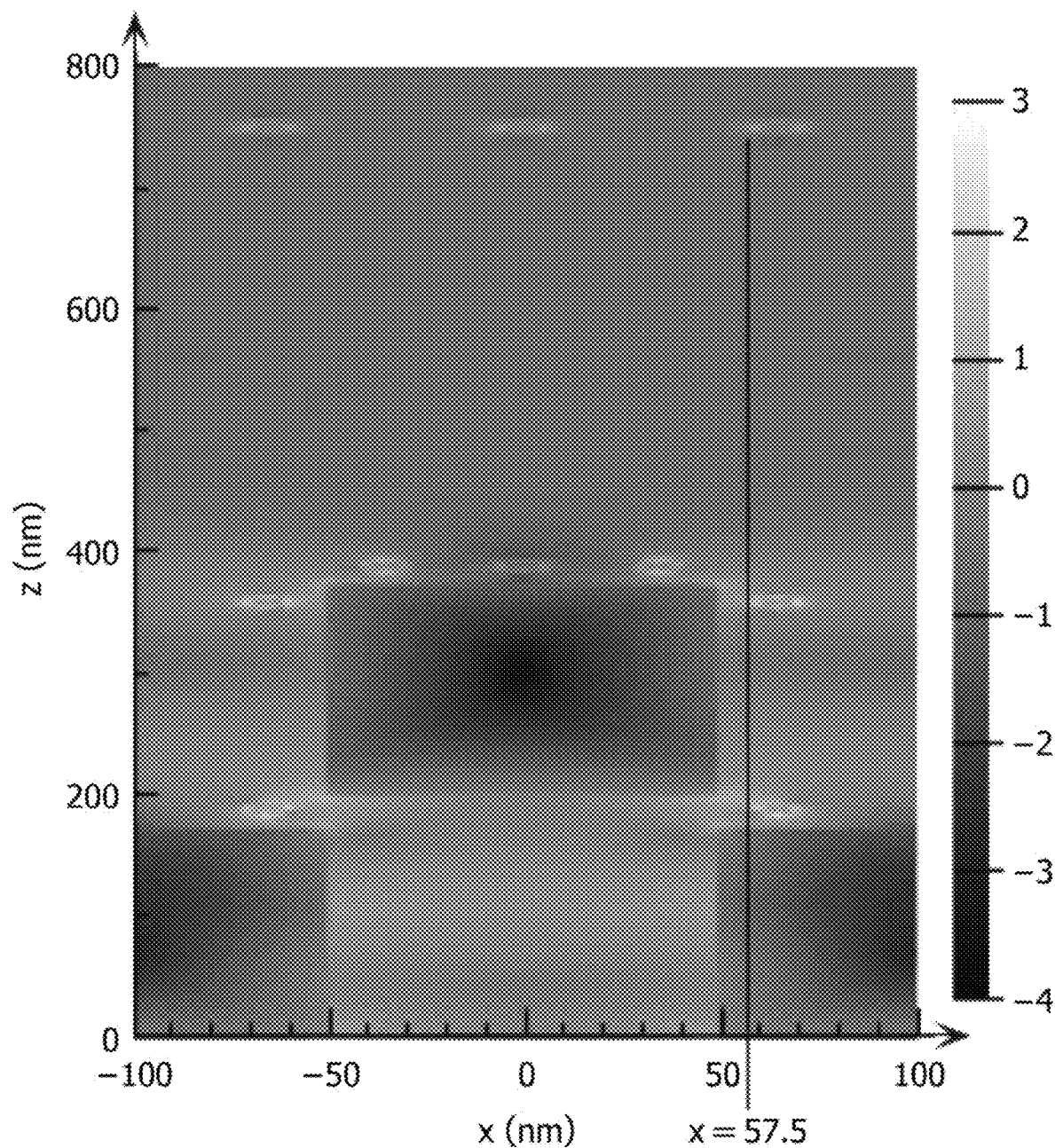
FIG. 9 is a distribution diagram of the square of electric field intensity in the periphery of a metal nanostructure according to an example.
Figure 10:
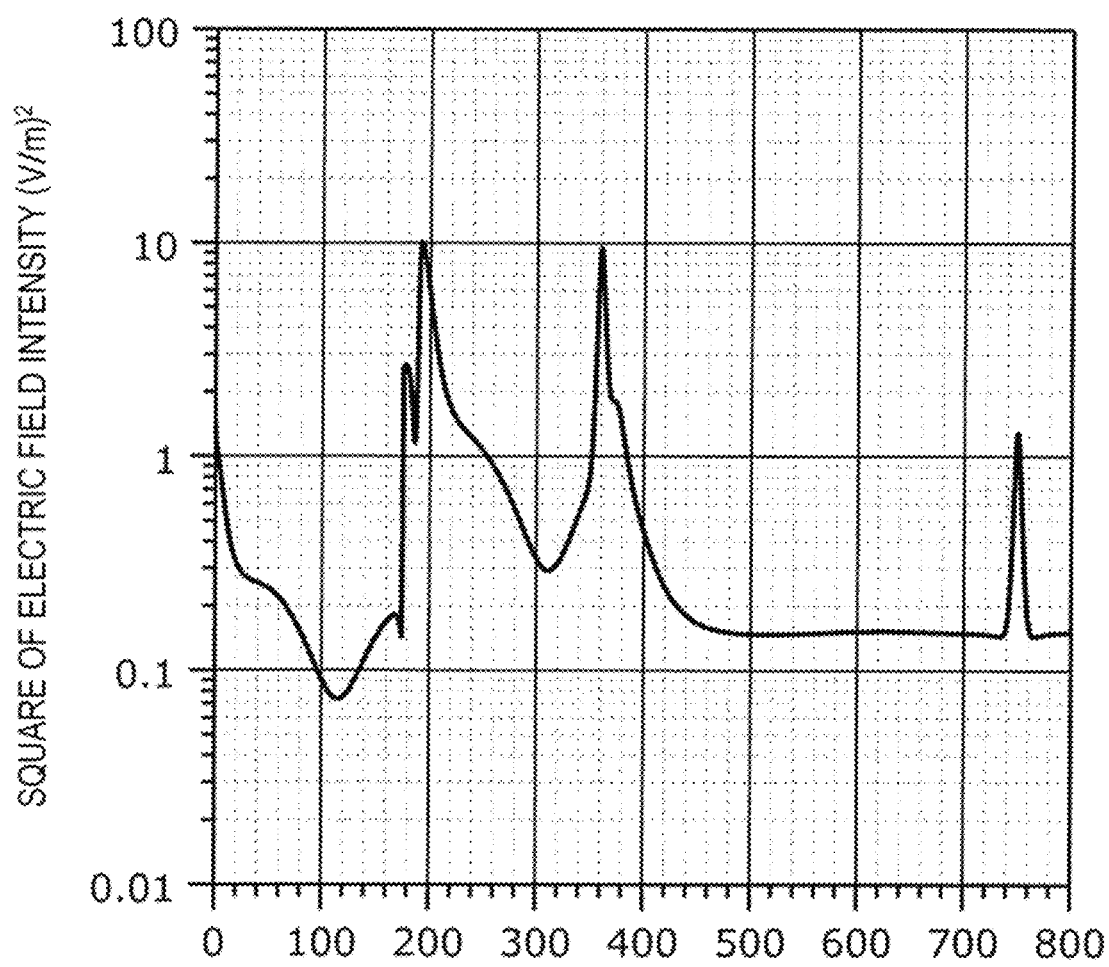
FIG. 10 is a graph showing positional dependence in a z direction of the square of electric field intensity in an example.

FIG. 8 to FIG. 10 each illustrate a result of simulation of electric-field distribution based on the metal nanostructure illustrated in FIG. 7 and the local surface plasmon resonance of the gold colloid by a FDTD method (finite-difference time-domain method). Here, data of the refractive index of water was used because the metal nanostructure and the gold colloid are present in the test solution 18.

First, to grasp the resonant property of local surface plasmon resonance, a reflection spectrum in a −z direction when the excitation light 19 is emitted in the z direction from the back surface side of the substrate 11 was calculated. FIG. 8 is a graph of the reflection spectrum of the metal nanostructure according to the example. Here, the polarization direction of the excitation light 19 is a direction (that is, the y direction) orthogonal to the line direction (that is, the x direction).

FIG. 8 shows depressions, which indicate local surface plasmon resonance, around wavelength=456 nm, 564 nm, and 830 nm. The gold colloid in water generated local surface plasmon resonance with wavelength=520 to 880 nm.

Then, xz-face distribution of the square of electric field intensity in the periphery of the metal nanostructure when the periphery of the metal nanostructure was irradiated with excitation light having a wavelength of 564 nm was calculated. FIG. 9 is a distribution diagram of the square of electric field intensity in the periphery of the metal nanostructure according to the example.

The square of the electric field intensity corresponds to the enhancement degree of fluorescence. These are distribution diagrams of the square $((V/m)^2)$ of electric field intensity in the periphery of the metal nanostructure when the excitation light 19 in which electric field intensity=1 (V/m) was emitted in the z direction. Here, the numerical values of the shaded bar (legend) are numerical values logarithmically indicating the square $((V/m)^2)$ of electric field intensity. In the shaded bar, 1 denotes 10 $(V/m)^2$, 2 denotes 100 $(V/m)^2$, −1 denotes $1/10$ $(V/m)^2$, and −2 denotes $1/100$ $(V/m)^2$.

As revealed in FIG. 9, regions (hotspots) in which the electric field was enhanced are seen around the corners of the linear projections and in the periphery of the gold colloid immobilized on the metal film 12 in the following locations.
(1) x=65 nm, z=190 nm
(2) x=65 nm, z=360 nm
(3) x=35 nm, z=390 nm
(5) x=−65 nm, z=190 nm
(6) x=−65 nm, z=360 nm
(7) x=−35 nm, z=390 nm FIG. 10 is a graph showing positional dependence of the square of electric field intensity in the z direction in the example. FIG. 10 shows positional dependence of electric field intensity in the z direction in the location of x=57.5 nm. In FIG. 10, a straight line indicating the location of x=57.5 nm is drawn. The location of x=57.5 nm is away by 2.5 nm from the gold colloid (diameter=10 nm) disposed in the location of x=65 nm and is in the vicinity of the fluorescent material 15. Therefore, the square of electric field intensity in the location of x=57.5 nm corresponds to the enhancement degree of fluorescence generated from the fluorescent material 15. Note that, in the location of x=−57.5 nm, an enhancement degree similar to that in the location of x=57.5 nm is obtainable.

In FIG. 10, the peak of the enhancement degree at z=175 nm was generated by, mainly, local surface plasmon resonance of the metal nanostructure. The peaks at z=190 nm and z=360 nm were generated by the local surface plasmon resonance of the gold colloid in addition to the local surface plasmon resonance of the metal nanostructure. The above local surface plasmon resonance enhances fluorescence generated from the labeled antibodies of the component B. The peak of the enhancement degree at z=750 nm was generated by the local surface plasmon resonance of the gold colloid.

This local surface plasmon resonance enhances fluorescence generated from the labeled antibodies of the component F. Note that the enhancement degree of the fluorescence of the component F was, however, approximately one tenth the enhancement degree of the fluorescence of the component B.

When the excitation light 19 is emitted from the surface side of the substrate 11, the square of electric field intensity in a region in which z>375 nm or more is 1 $((V/m)^2)$ in average. In contrast, as illustrated in FIG. 10, in the present example, the square of electric field intensity is 1 $((V/m)^2)$ or less in the region in which z>375 nm or more, in which no gold colloid is present, and decreases to approximately 0.15 $((V/m)^2)$.

If a distance between the substrate 11 and the transparent cover 17 is not approximately 10 μm or more, it is difficult to hold the test solution 18. The thickness of the test solution 18 in the z direction is thus approximately 10 μm or more. Considering the above, the square of electric field intensity of a most portion of the test solution 18 is approximately 0.15 $((V/m)^2)$. Therefore, in the present example, it is possible to reduce the enhancement degree of the scattered light and the fluorescence of substances coexisting with the test solution 18 to be substantially one seventh of that in existing techniques.

Moreover, the width of an enhancement region in which the square of electric field intensity is 1 or more in the periphery of the metal nanostructure is approximately 50 nm, which is less than the width of an enhancement region generated by evanescent waves by approximately 1 digit. Consequently, it is possible to reduce an adverse influence exerted on the detection of a detection object substance by fluorescence from the component F and scattered light and fluorescence of the coexisting substances.

In addition, as shown in FIG. 9, the square of electric field intensity is also similarly low in locations, except for the periphery of the gold colloids, other than the location of x=57.5 nm, and it is found to be possible to suppress the fluorescence of the component F and the scattered light and the fluorescence of the coexisting substances from being enhanced.

As above, it is possible, by emitting the excitation light 19 from the back surface side of the substrate having the metal nanostructure 30, to suppress the fluorescence of the component F and the scattered light and the fluorescence of the coexisting substances from being enhanced, which enables detection of a detection object substance to be performed with high accuracy without performing BF separation.

Another Embodiment

The detection apparatus according to one aspect or aspects of the present disclosure has been described above on the basis of an embodiment; the present disclosure is, however, not limited by this embodiment. As long as not deviating from the spirit of the present disclosure, the present embodiment subjected to various modifications conceivable by a person skilled in the art or forms constituted by a combination of constituent elements in different embodiments should be also included in the range of the one aspect or the aspects of the present disclosure.

For example, in the aforementioned embodiment, the light transmissive portion 32 is a region of the surface of the substrate 11 not covered with the metal film 12; the light transmissive portion 32 is, however, not limited thereto. The light transmissive portion 32 may have any configuration provided that the excitation light 19 is transmitted therethrough. For example, the light transmissive portion 32 may be a region of the surface of the substrate 11 covered with the metal film thinner than the metal film on the non-light transmissive portion 33. For example, the light transmissive portion 32 may be a region covered with a metal film having a film thickness of approximately 50 nm or less when the metal film is made of gold, silver, or aluminum. When the metal film has a thickness of approximately 50 nm, excitation light is transmitted through the region covered with the metal film. The region thus functions as the light transmissive portion 32. When the light transmissive portion 32 is a region of the surface of the substrate 11 covered with the thin metal film, sputtering or the like is usable as a film forming method for the metal film.

In the aforementioned embodiment, the labeled antibodies 16 bind with the gold colloid 27; the labeled antibodies 16, however, not necessarily bind with the gold colloid 27. In other words, it is possible, without using the gold colloid 27, to suppress the fluorescence of the component F and enhancement thereof by irradiating the metal nanostructure 30 according to the aforementioned embodiment with the excitation light 19 from the back surface side of the substrate 11. It is thus possible to improve accuracy in detection of a detection object substance without BF separation.

In the aforementioned embodiment, the gold colloid 27 is used; however, other metal colloid particles may be used. For example, as an alternative to the gold colloid 27, colloid particles of silver or aluminum may be used.

In the aforementioned embodiment, the metal nanostructure 30 has the line-and-space structure; the metal nanostructure 30 is, however, not limited thereto. For example, the metal nanostructure 30 may have rectangular column shaped projections disposed in a matrix form.

Figure 11:
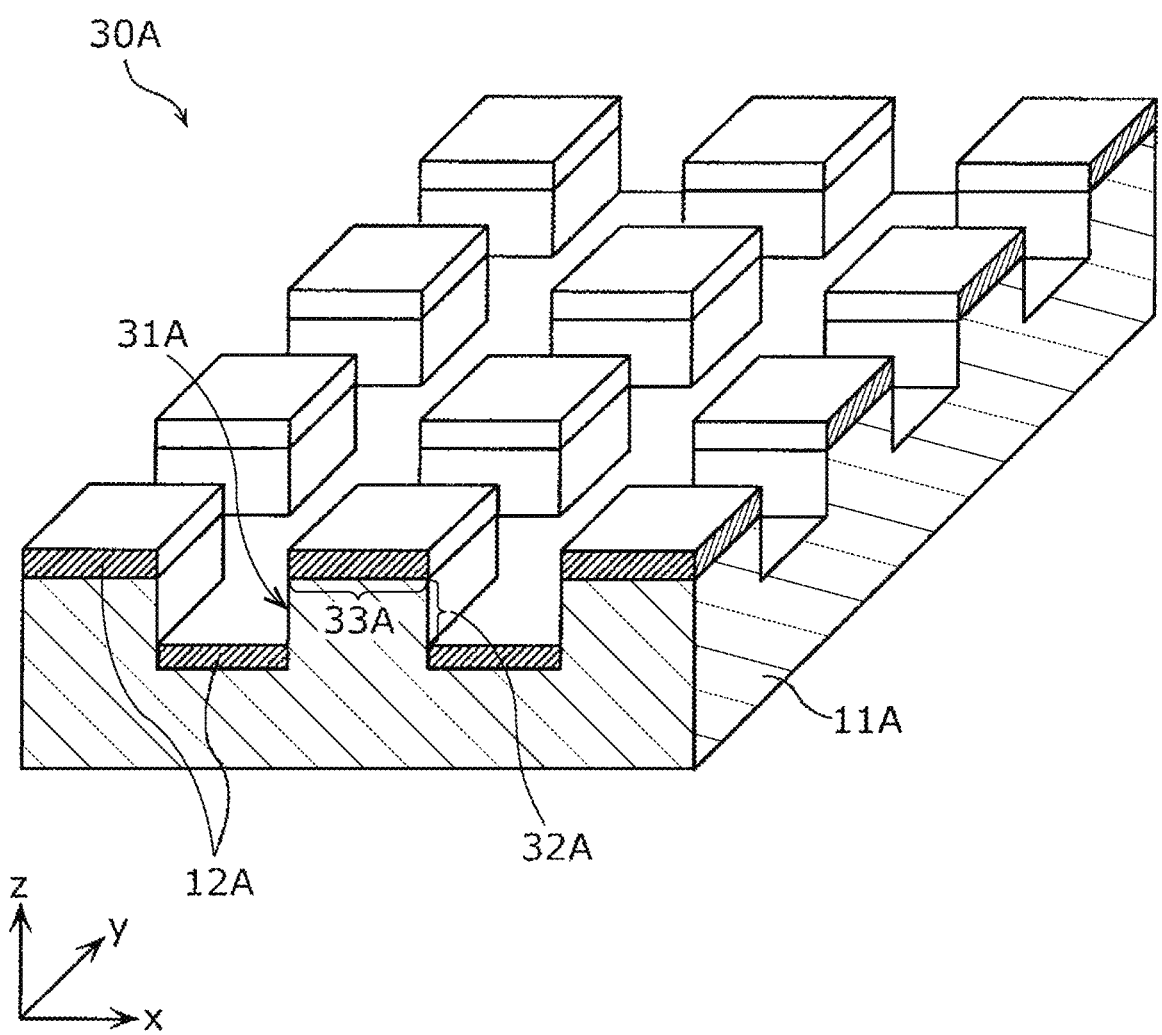
FIG. 11 is a perspective view of a metal nanostructure according to another embodiment.

FIG. 11 is a perspective view of a metal nanostructure 30A according to another embodiment. The metal nanostructure 30A is formed by a substrate 11A and a metal film 12A. The metal film 12A includes rectangular column shaped projections 31A. A non-light transmissive portion 33A, which is a region covered with the metal film 12A, is formed on the upper surfaces (xy faces) of the projections 31A and on the bottom surfaces (xy faces) of grooves between the projections 31A. In addition, a light transmissive portion 32A, which is a region not covered with the metal film 12A, is formed on the side surfaces (xz faces and yz faces) of the projections 31A.

In FIG. 11, the projections each have a rectangular column shape; however, the shape thereof may have another shape. For example, the projections may have a circular cylinder shape or a hexagonal cylinder shape.

In the aforementioned embodiment, the light transmissive portion 32 is formed in regions in the side surfaces of the projections; however, the light transmissive portion 32 is not limited thereto. For example, the light transmissive portion 32 may be formed in regions in the upper surfaces of the projections or in the bottom surfaces of the grooves between the projections.

In the aforementioned embodiment, the lenses 23 and 24 and the long-path filter 25 are included in the detection apparatus; however, the lenses 23 and 24 and the long-path filter 25 are not necessarily included therein. For example, the photodetector 42 may realize the functions of the lenses 23 and 24 and the long-path filter 25.

In the aforementioned embodiment, the metal nanostructure 30 is formed by a resin substrate and a metal film; however, the metal nanostructure 30 is not limited thereto. For example, the metal nanostructure 30 may be a metal substrate that includes projections. In this case, a thick region of the metal substrate may function as the non-light transmissive portion, and a thin region of the metal substrate may function as the light transmissive portion.

The present disclosure is usable for a sensor device that measures concentration of a pathogen-derived protein and the like.

What is claimed is:

1. A detection apparatus comprising:
a substrate having a first major face and a second major face opposite to the first major face;
a metal microstructure disposed on the first major face and on which a first specific binding substance having a property of binding with a detection object substance is immobilized, the metal microstructure generating a surface plasmon by being irradiated with excitation light;
an introducer that introduces a second specific binding substance and a sample containing the detection object substance into the metal microstructure, the second specific binding substance having a property of binding with the detection object substance and being labeled with a fluorescent material;
a light irradiator that irradiates the metal microstructure into which the second specific binding substance and the sample have been introduced with the excitation light from a side of the second major face of the substrate, a distance between the light irradiator and the second major face being shorter than a distance between the light irradiator and the first major face; and
a detector that detects the detection object substance based on fluorescence generated from the fluorescent material in response to irradiation of the excitation light, wherein
the metal microstructure includes a light transmissive portion that transmits, to a side of the first major face, the excitation light emitted from the side of the second major face,
the metal microstructure further includes a non-light transmissive portion having lower transparency to the excitation light than the light transmissive portion,
the substrate has a property of transmitting the excitation light,
the non-light transmissive portion is a region in the first major face covered with a metal film, and
the light transmissive portion is a region in the first major face not covered with the metal film or a region of the first major face covered with the metal film thinner than the metal film on the non-light transmissive portion.

2. The detection apparatus according to claim 1, wherein the metal microstructure includes projections, and
the light transmissive portion is regions in respective side surfaces of the projections.

3. The detection apparatus according to claim 2, wherein the metal microstructure has a line-and-space structure, and
each of the projections has a linear shape.

4. The detection apparatus according to claim 1, wherein the metal film is formed of silver.

5. The detection apparatus according to claim 1, wherein the second specific binding substance is bound with metal colloid particles.

6. The detection apparatus according to claim 5, wherein the metal colloid particles are gold colloid particles.

* * * * *